United States Patent
Willis

(10) Patent No.: US 12,427,319 B2
(45) Date of Patent: *Sep. 30, 2025

(54) PULSE DELIVERY DEVICE INCLUDING SLEW RATE DETECTOR, AND ASSOCIATED SYSTEMS AND METHODS

(71) Applicant: EBR Systems, Inc., Sunnyvale, CA (US)

(72) Inventor: Nathaniel Parker Willis, Sunnyvale, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/302,639

(22) Filed: Apr. 18, 2023

(65) Prior Publication Data

US 2023/0355989 A1 Nov. 9, 2023

Related U.S. Application Data

(63) Continuation of application No. 16/557,367, filed on Aug. 30, 2019, now Pat. No. 11,654,287.

(51) Int. Cl.
*A61N 1/362* (2006.01)
*A61N 1/378* (2006.01)
(Continued)

(52) U.S. Cl.
CPC ............ *A61N 1/362* (2013.01); *A61N 1/3787* (2013.01); *A61N 1/39622* (2017.08); *H02M 3/07* (2013.01);
(Continued)

(58) Field of Classification Search
CPC ....................................................... A61N 1/362
(Continued)

(56) References Cited

U.S. PATENT DOCUMENTS 3,659,615 A  5/1972 Enger
3,735,756 A  5/1973 Richards
(Continued)

FOREIGN PATENT DOCUMENTS

DE  4330680 A1  3/1995
GB  1146976 A  3/1969
(Continued)

OTHER PUBLICATIONS

European Office Action mailed Apr. 13, 2012 for Application No. 09725884.2.
(Continued)

*Primary Examiner* — Nicole F Johnson
(74) *Attorney, Agent, or Firm* — Perkins Coie LLP

(57) ABSTRACT

The present technology is generally directed to implantable medical device systems configured to provide cardiac resynchronization therapy. In some embodiments, the implantable medical device system comprises a housing, electrodes carried by the housing, a transducer configured to produce input voltage signals in response to ultrasound energy, and a circuit configured to provide, via an electrical pathway, output voltage signals based on the input voltage signals. The circuit comprises a movable switch, and a slew rate detector configured to detect whether a voltage rate of an individual pulse of the input voltage signals exceeds a predetermined threshold voltage rate. The circuit is configured to move the switch to an open position in response to the detected voltage rate exceeding the predetermined threshold voltage rate.

19 Claims, 9 Drawing Sheets

(51) Int. Cl.
    *A61N 1/39*           (2006.01)
    *H02M 3/07*        (2006.01)
    *H02N 2/18*         (2006.01)
    *A61B 8/12*         (2006.01)

(52) U.S. Cl.
    CPC ............... *H02N 2/181* (2013.01); *A61B 8/12* (2013.01); *H02M 3/071* (2021.05)

(58) Field of Classification Search
    USPC ......................................................... 607/33
    See application file for complete search history.

(56) References Cited

U.S. PATENT DOCUMENTS

| | | |
|---|---|---|
| 3,767,971 A | 10/1973 | Patrick, Jr. |
| 4,050,004 A | 9/1977 | Greatbatch |
| 4,102,344 A | 7/1978 | Conway et al. |
| 4,991,583 A | 2/1991 | Silvian |
| 5,193,539 A | 3/1993 | Schulman |
| 5,266,746 A | 11/1993 | Nishihara |
| 5,314,453 A | 5/1994 | Jeutter |
| 5,545,183 A | 8/1996 | Altman |
| 5,749,909 A | 5/1998 | Schroeppel et al. |
| 5,833,710 A | 11/1998 | Jacobson |
| 6,140,740 A | 10/2000 | Porat |
| 6,327,498 B1 | 12/2001 | Kroll |
| 6,504,286 B1 | 1/2003 | Porat |
| 6,628,989 B1 | 9/2003 | Penner |
| 6,654,638 B1 | 11/2003 | Sweeney |
| 6,764,446 B2 | 7/2004 | Wolinsky |
| 6,771,785 B2 | 8/2004 | Pompei |
| 7,283,874 B2 | 10/2007 | Penner |
| 7,489,967 B2 | 2/2009 | Von Arx et al. |
| 7,522,962 B1 | 4/2009 | Doron et al. |
| 7,542,804 B2 | 6/2009 | Mandell |
| 7,606,621 B2 | 10/2009 | Brisken |
| 7,610,092 B2 | 10/2009 | Cowan et al. |
| 7,865,247 B2 | 1/2011 | Smith |
| 7,983,748 B2 | 7/2011 | Ruse |
| 8,364,276 B2 | 1/2013 | Willis |
| 8,369,960 B2 | 2/2013 | Tran |
| 8,588,926 B2 | 11/2013 | Moore et al. |
| 9,180,285 B2 | 11/2015 | Moore |
| 9,343,654 B2 | 5/2016 | Moore |
| 9,731,138 B1 | 8/2017 | Stadler |
| 9,981,138 B2 | 5/2018 | Willis |
| 10,052,493 B2 | 8/2018 | Moore |
| 10,512,785 B2 | 12/2019 | Moore |
| 10,806,938 B2 | 10/2020 | Moore |
| 11,654,287 B2 | 5/2023 | Willis et al. |
| 2002/0077673 A1 | 6/2002 | Penner |
| 2003/0104269 A1 | 6/2003 | Gan et al. |
| 2004/0172083 A1 | 9/2004 | Penner |
| 2004/0204744 A1 | 10/2004 | Penner |
| 2005/0154294 A1 | 7/2005 | Uchiyama |
| 2005/0165456 A1 | 7/2005 | Mann |
| 2006/0004424 A1 | 1/2006 | Loeb et al. |
| 2006/0136004 A1 | 6/2006 | Cowan |
| 2006/0136005 A1 | 6/2006 | Brisken |
| 2007/0027580 A1 | 2/2007 | Cowan et al. |
| 2007/0055184 A1 | 3/2007 | Echt et al. |
| 2007/0167988 A1 | 7/2007 | Cernasov |
| 2007/0233200 A1 | 10/2007 | Maschke |
| 2007/0282383 A1 | 12/2007 | Koyama |
| 2007/0293895 A1 | 12/2007 | Cowan |
| 2008/0021504 A1 | 1/2008 | McCabe et al. |
| 2008/0021509 A1 | 1/2008 | Mi et al. |
| 2008/0243210 A1 | 10/2008 | Doron et al. |
| 2008/0269818 A1 | 10/2008 | Sullivan |
| 2008/0294208 A1 | 11/2008 | Willia |
| 2008/0312720 A1 | 12/2008 | Tran |
| 2012/0203306 A1 | 8/2012 | Sarvazyan |
| 2014/0142444 A1 | 5/2014 | Ngo et al. |
| 2017/0281954 A1* | 10/2017 | Reinke ................. A61N 1/3787 |
| 2021/0146143 A1 | 5/2021 | Moore et al. |
| 2024/0017079 A1 | 1/2024 | Moore et al. |

FOREIGN PATENT DOCUMENTS

| | | |
|---|---|---|
| WO | 2005009535 A1 | 2/2005 |
| WO | 2007016581 A2 | 2/2007 |
| WO | 2007016581 A3 | 5/2007 |
| WO | 2007149936 A2 | 12/2007 |
| WO | 2007149936 A3 | 10/2008 |
| WO | 2009120785 A2 | 10/2009 |
| WO | 2009120785 A3 | 12/2009 |
| WO | 2011112865 A1 | 9/2011 |

OTHER PUBLICATIONS

European Search Report mailed Apr. 18, 2012 for Application No. 12151794.0.
European Search Report mailed Jun. 27, 2011 for EP Application No. 09725884.2.
European Search Report mailed Sep. 26, 2013 for EP Application No. 11754116.9.
Extended European Search Report mailed Jan. 14, 2021 for European Patent Application No. 20193483.3, 6 pages.
Final Office Action mailed Dec. 22, 2014 for U.S. Appl. No. 13/648,027.
Final Office Action mailed Dec. 30, 2022 for U.S. Appl. No. 17/030,846, 8 pages.
International Search Report and Written Opinion mailed May 19, 2011 for PCT/US2011/027985.
International Search Report and Written Opinion mailed May 25, 2009 for PCT/US2009/038258.
Non-Final Office Action mailed Jan. 12, 2015 for U.S. Appl. No. 14/059,228.
Non-Final Office Action mailed Feb. 21, 2020 for U.S. Appl. No. 16/051,338.
Non-Final Office Action mailed Jun. 11, 2012 for U.S. Appl. No. 12/721,483.
Non-Final Office Action mailed Jun. 13, 2014 for U.S. Appl. No. 13/648,027.
Non-Final Office Action mailed Jun. 24, 2022 for U.S. Appl. No. 17/030,846, 8 pages.
Non-Final Office Action mailed Jun. 30, 2022 for U.S. Appl. No. 16/557,367, 10 pages.
Non-Final Office Action mailed Aug. 24, 2017 for U.S. Appl. No. 15/138,046.
Non-Final Office Action mailed Oct. 26, 2021 for U.S. Appl. No. 16/557,367, 8 pages.
Notice of Allowance mailed Jan. 20, 2016 for U.S. Appl. No. 14/883,925.
Notice of Allowance mailed Jan. 20, 2023 for U.S. Appl. No. 16/557,367, 8 pages.
Notice of Allowance mailed Jan. 30, 2018 for U.S. Appl. No. 13/648,027.
Notice of Allowance mailed Mar. 9, 2023 for U.S. Appl. No. 17/030,846, 7 pages.
Notice of Allowance mailed Apr. 18, 2018 for U.S. Appl. No. 15/138,046.
Notice of Allowance mailed May 24, 2019 for U.S. Appl. No. 16/250,943.
Notice of Allowance mailed Jun. 17, 2020 for U.S. Appl. No. 16/051,338.
Notice of Allowance mailed Jul. 22, 2013 for U.S. Appl. No. 13/734,680.
Notice of Allowance mailed Jul. 31, 2015 for U.S. Appl. No. 14/059,228.
Notice of Allowance mailed Aug. 30, 2019 for U.S. Appl. No. 16/250,943.
Notice of Allowance mailed Sep. 26, 2012 for U.S. Appl. No. 12/721,483.
Notice of Allowance mailed Sep. 28, 2012 for U.S. Appl. No. 12/721,483.

(56) References Cited

OTHER PUBLICATIONS

Non-Final Office Action mailed Dec. 19, 2024 for U.S. Appl. No. 18/331,781, 11 pages.
Non-Final Office Action mailed May 23, 2024 for U.S. Appl. No. 18/331,781, 91 pages.

* cited by examiner

PULSE DELIVERY DEVICE INCLUDING SLEW RATE DETECTOR, AND ASSOCIATED SYSTEMS AND METHODS

CROSS-REFERENCE TO RELATED APPLICATIONS

This application is a continuation of U.S. patent application Ser. No. 16/557,367, titled "PULSE DELIVERY DEVICE INCLUDING SLEW RATE DETECTOR, AND ASSOCIATED SYSTEMS AND METHODS," and filed Aug. 30, 2019, which is incorporated by reference herein in its entirety.

This application is also related to U.S. patent application Ser. No. 12/721,483, now U.S. Pat. No. 8,364,276, titled "OPERATION AND ESTIMATION OF OUTPUT VOLTAGE OF WIRELESS STIMULATORS," and filed Mar. 10, 2010, which is incorporated by reference herein in its entirety.

TECHNICAL FIELD

The disclosure relates generally to implantable medical devices, and in particular embodiments, to implantable medical devices configured to provide cardiac resynchronization therapy.

BACKGROUND

In healthy hearts, electrical impulses signal the left and right ventricles to beat in a synchronized manner. Conduction defects associated with the electrical pathways of the heart cause asynchronous contraction of the ventricles. One solution to correct these asynchronous defects uses an implanted cardiac pacemaker electrically coupled to leads for delivering electrical stimulation pulses to the right and left ventricles. The right ventricular lead is placed on the inner surface (endocardium) of the right ventricle. To avoid the risk of stroke, the LV lead is typically routed from the right ventricle through the coronary sinus vein and around the back of the heart to access the outer surface (epicardium) of the left ventricle. In some patients, though, the epicardial location of the leads on the left ventricle does not adequately synchronize the heartbeat. To overcome this problem, a wireless electrode can be implanted on the inner surface (endocardium) of the left ventricle. The wireless electrode can be configured to receive ultrasound energy from a transmitter positioned outside the heart (e.g., in the chest area) and convert the ultrasound energy to electrical energy to pace the left ventricle via endocardial stimulation. The wireless electrode can be used in conjunction with other pacemakers that stimulate the right ventricle. Such wireless endocardial stimulation can provide more effective pacing, relative to epicardial pacing, to provide better synchronization of the heartbeat.

One issue associated with ultrasound-based wireless electrodes is when ultrasound energy signals other than those intended for cardiac pacing are present. For example, patients having implanted leadless pacemakers often undergo diagnostic ultrasound imaging procedures after implantation, e.g., to verify whether the electrodes and/or pacemakers were implanted correctly or to assess the mechanical function of the heart. Other examples of ultrasound energy signals include other types of diagnostic or therapeutic ultrasound, such as ultrasound guidance for biopsies, high-intensity ultrasound procedures, etc. Such diagnostic and therapeutic procedures use ultrasound energy signals that could energize the wireless electrodes and inadvertently stimulate the heart.

DETAILED DESCRIPTION

The present technology is directed generally to implantable medical devices configured to inhibit selected signals from being delivered to a patient's heart, and associated systems and methods. More specifically, embodiments of the present technology are directed to implantable medical devices configured to inhibit energy signals having a voltage rate and/or a pulse duration outside a predetermined threshold range from being delivered to a patient's heart.

General aspects of the environments in which the disclosed technology operates are described below under Heading 1.0 ("Overview") with reference to FIGS. 1 and 2A-2C. Some embodiments of the technology are described further under Heading 2.0 ("Representative Embodiments") with reference to FIGS. 3-9. While the present technology is described in the environment of stimulating the heart, one with skill in the art would recognize that one or more aspects of the present technology are applicable to other implantable devices configured to treat other areas of the human body.

1.0 Overview

Figure 1:
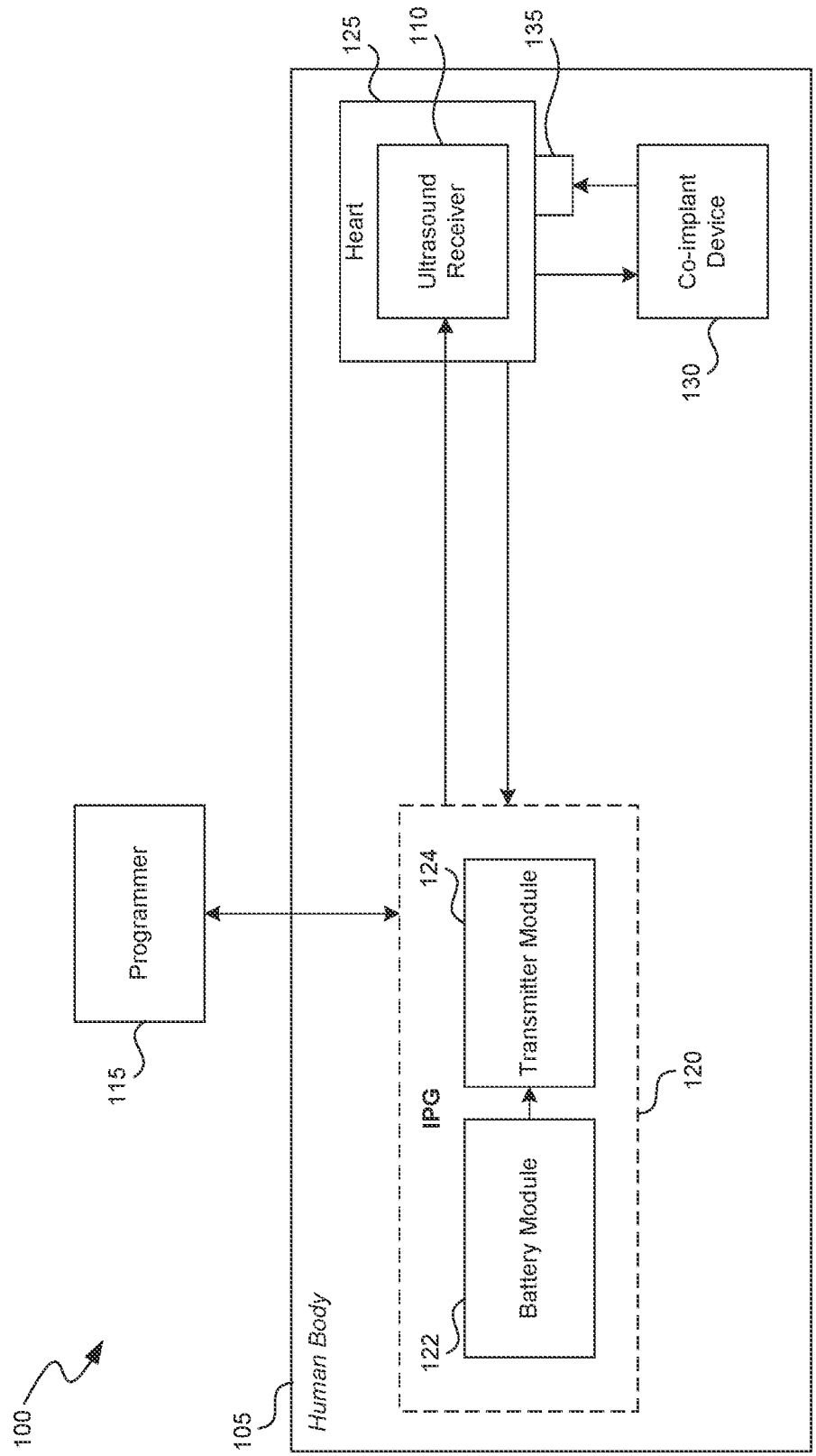
FIG. 1 is a schematic diagram of a cardiac resynchronization therapy system including a receiver-stimulator for delivering stimulation pulses to a patient's heart, in accordance with the present technology.

FIG. 1 is a schematic diagram of a cardiac resynchronization therapy system 100 ("system 100") including a receiver-stimulator 110 ("Ultrasound Receiver 110") for delivering stimulation pulses to a patient's heart 125, in accordance with embodiments of the present technology. The system 100 can further include a programmer 115 and an implantable pulse generator (IPG) 120 in operable communication (e.g., wireless and/or radio communication) with the programmer 115. The IPG 120 can include a battery module 122 and a transmitter module 124 operably coupled to and powered via the battery module 122. The receiver 110 is configured to receive ultrasound energy signals from the IPG 120. As shown in FIG. 1, the programmer 115 can be positioned outside the human body 105, the IPG 120 can be positioned within the human body (e.g., in the chest area), and the receiver 110 is positioned in and/or on the heart 125 (e.g., in the left ventricle, the right ventricle, or proximate area). The system 100 can further include a co-implant device 130 (e.g., an implantable cardioverter defibrillator (ICD) or pacemaker) coupled to pacing leads 135 for delivering stimulation pulses to one or more portions of the heart 125 other than the area stimulated by the receiver 110. Alternatively the co-implant 130 could be a leadless pacemaker which is implanted directly into the heart to eliminate the need for separate pacing leads 135. The co-implant device 130 and IPG 120 are configured to operate in tandem and deliver stimulation signals to the heart 125 to cause a synchronized heartbeat. As shown in FIG. 1, the IPG 120 can receive signals (e.g., electrocardiogram signals) from the heart 125 to determine information related to the heart, such as heart rate, heart rhythm, including the output of the co-implant pacing leads located in the heart. The signals received from the heart 125 can be used to adjust the ultrasound energy signals delivered to the receiver 110. Additionally, the programmer 115 can receive signals from the heart 125, such as signals corresponding to the stimulation signals delivered to the heart 125 via the receiver 110. Accordingly, the programmer 115 and/or the IPG 120 can function in part as a sensing device.

The programmer 115 and/or IPG 120 can include a machine-readable (e.g., computer-readable) or controller-readable medium containing instructions for generating and transmitting suitable stimulation signals. The programmer 115 and/or IPG 120 can include one or more processor(s), memory unit(s), and/or input/output device(s). Accordingly, the process of providing stimulation signals and/or executing other associated functions can be performed by computer-executable instructions contained by, on or in computer-readable media located at the programmer 115 and/or the IPG 120. Further, the programmer 115 and/or the IPG 120 may include dedicated hardware, firmware, and/or software for executing computer-executable instructions that, when executed, perform any one or more methods, processes, and/or sub-processes described herein; e.g., the methods, processes, and/or sub-processes described with reference to FIGS. 3-9 below. The dedicated hardware, firmware, and/or software also serve as "means for" performing the methods, processes, and/or sub-processes described herein.

2.0 Representative Embodiments

As previously described, an issue associated with conventional implantable wireless electrodes is the inability of the electrodes to distinguish between ultrasound energy signals intended for cardiac pacing and those that are for other functions, such as diagnostic ultrasound. For example, ultrasound diagnostic signals, such as those used for imaging (e.g., transthoracic echo (TTE) imaging signals), are generally not intended for cardiac pacing, but conventional electrodes may not adequately distinguish the diagnostic energy signals from the stimulation signals intended for cardiac pacing. Embodiments of the present technology overcome this deficiency of conventional wireless electrodes by blocking or otherwise limit signals other than cardiac pacing/stimulation signals, and thereby preventing them from being delivered to the heart.

Figure 2A:
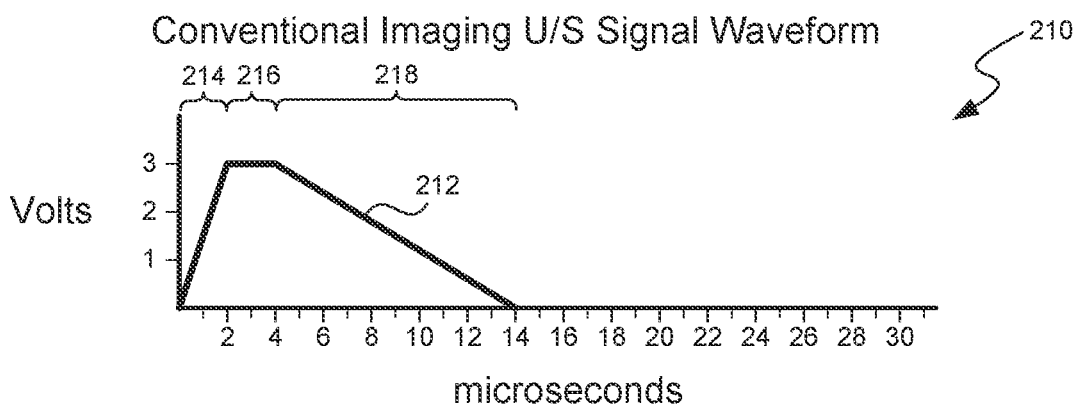
FIGS. 2A and 2B are plots of the transduced and rectified response to conventional imaging waveforms.
Figure 2B:
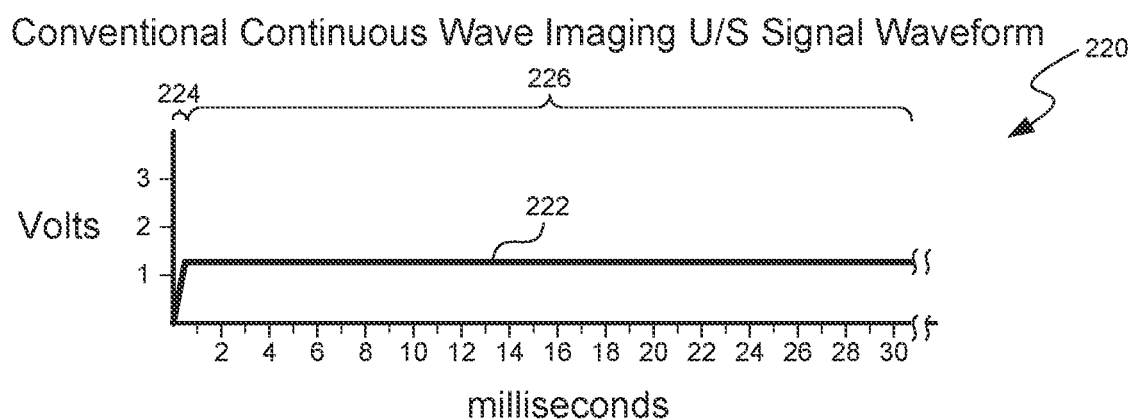
Figure 2C:
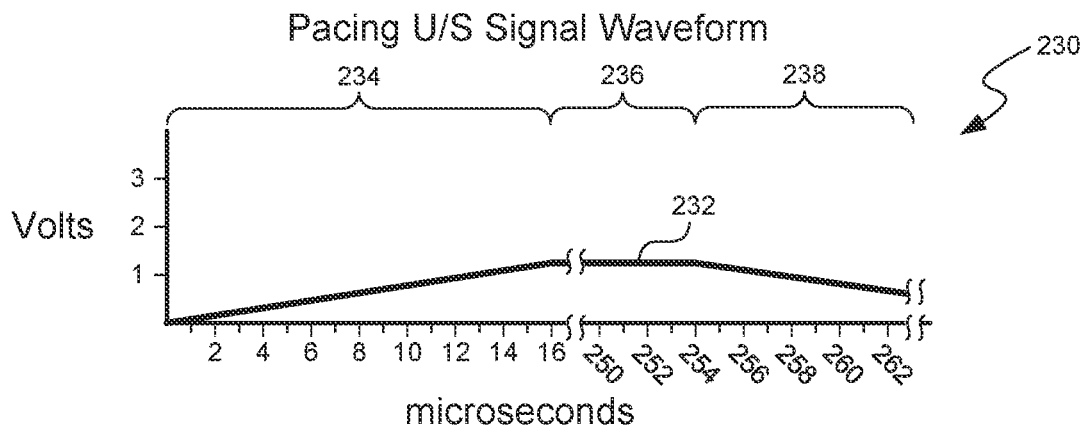
FIG. 2C is a plot of the transduced and rectified response to a waveform in accordance with the present technology.

FIGS. 2A and 2B are plots of the transduced and rectified response to the ultrasound input ("receiver response") when exposed to ultrasound energy from conventional imaging waveforms, and FIG. 2C is a plot of the transduced and rectified response an ultrasound waveform in accordance with embodiments of the present technology. Specifically, FIG. 2A is a plot 210 illustrating the change in voltage over time (microseconds) of a waveform 212 in response to a conventional imaging ultrasound signal, FIG. 2B is a plot 220 illustrating the change in voltage over time (milliseconds) of a waveform 222 in response to a conventional continuous wave ultrasound imaging signal, and FIG. 2C is a plot 230 illustrating the change in voltage over time (microseconds) of a waveform 232 in response to an ultrasound signal waveform 232 ("waveform") in accordance with the present technology. Referring first to FIG. 2A, the waveform 212 includes a first portion 214 in which the voltage of the waveform 212 rises at a rate of about 1.5 V/µs, a second portion 216 in which the voltage of the waveform 212 remains constant, and a third portion 218 in which the voltage of the waveform 212 falls at a rate of about 0.3 V/µs. Referring next to FIG. 2B, the waveform 222 includes a first portion 224 in which the waveform 222 rises at a rate of about 1.5 V/ms, and a second portion in which the voltage of the waveform 222 remains constant, e.g., for more than 20 milliseconds (ms) (e.g., 50 ms, 100 ms, or 200 ms). Referring next to FIG. 2C, the waveform 232 includes a first portion 234 in which the voltage of the waveform 232 rises at a rate of about 0.075V/us and a second portion 236 in which the voltage of the waveform 232 remains constant, and a third portion 238 in which the voltage of the waveform 232 falls as a rate of about 0.075 V/µs. The waveform 232 can generally correspond to a pacing pulse. A query pulse can generally correspond to the first portion 234 and third portion 238 of the waveform 232, but may include a shorter (e.g., 2 µs) second portion 236. In operation, a typical voltage signal includes multiple query pulses delivered, e.g., from the IPG 120 to the receiver 110 (FIG. 1), and a pacing pulse delivered after the query pulses.

The pacing waveform 232 of the present technology has different characteristics relative to each of the conventional diagnostic waveforms 212 and 222. For example, the rise rate of the first portion 214 of the conventional diagnostic waveform 212 is about twenty times greater than the rise rate of the first portion 234 of the pacing waveform 232 of the present technology. As another example, the pulse duration partially illustrated by the second portion 226 of the conventional diagnostic waveform 222 is significantly longer than the pulse duration of the pacing waveform 232 of the present technology. As described in more detail below, these different characteristics between the conventional diagnostic waveforms 212, 222 compared to the pacing waveform 232 of the present technology can be used to block or otherwise limit imaging and other signals not intended to be used for cardiac pacing from being delivered to the patient in the form of electrical stimulation.

Figure 3:
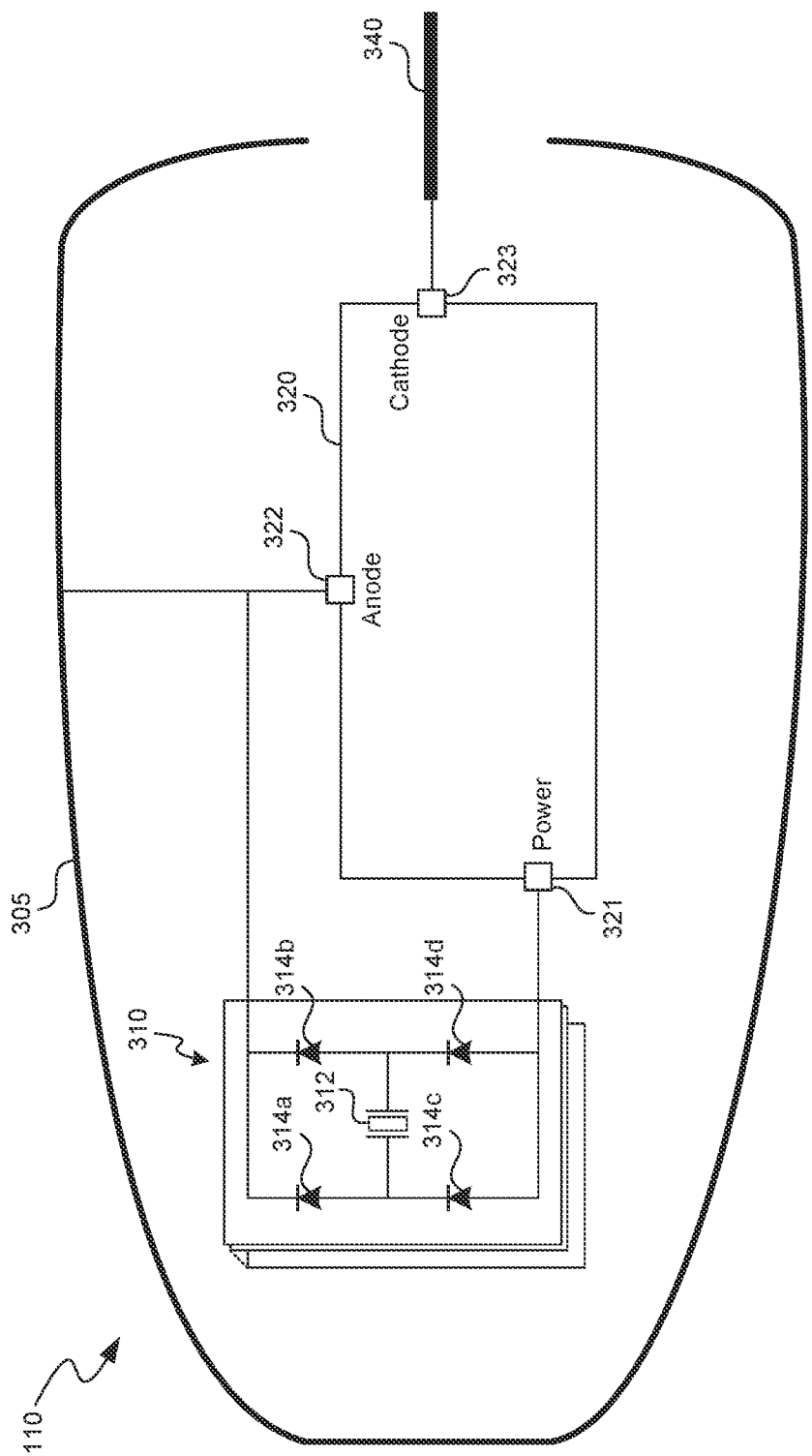
FIG. 3 is schematic diagram of the receiver-stimulator shown in FIG. 1, in accordance with the present technology.

FIG. 3 is a schematic diagram of the receiver 110 shown in FIG. 1, in accordance with embodiments of the present technology. As shown in FIG. 3, the receiver 110 includes a plurality of transducer and rectifier component(s) 310 ("components 310"), a circuit 320 electrically coupled to the components 310, a terminal 340 electrically coupled to the circuit 320, and a housing 305 containing the components 310 and the circuit 320. The circuit 320 can further include (a) a first pin 321 corresponding to input voltage or power to the circuit 320 and electrically connected to the components 310 via a first pathway, (b) a second pin 322 corresponding to an anode electrode and electrically connected to the components 310 via a second pathway, and (c) a third pin 323 corresponding to a cathode electrode and electrically connected to the terminal 340. As shown in FIG. 3, the second pin 322 corresponding to the anode electrode can be electrically connected to the housing 305. Accordingly, the outer surface of the housing 305 can define the electrode, and the terminal 340 can define a tip electrode. In some embodiments, the circuit 320 can comprise a die having a first dimension (e.g., width) of about 500 micrometers or less, a second dimension (e.g., length) of about 1500 micrometers or less, and a third dimension (e.g., thickness) of about 250 micrometers or less.

The components 310 are wired in parallel to one another, and each can include one or more piezoelectric element(s) 312 or transducers (only a single piezoelectric element is shown in FIG. 3), and diodes 314a-d (collectively referred to as "diodes 314") configured as a bridge rectifier electrically coupled to the piezoelectric element(s) 312. Alternatively the components 310 could be wired in series or a combination of series and parallel wiring to tune the source impedance and voltage output level. The piezoelectric element(s) 312 respond to ultrasound energy transmissions, including those transmitted from the IPG 120 (FIG. 1) and intended for cardiac pacing, as well as diagnostic (e.g., imaging) ultrasound energy transmissions not intended for cardiac pacing. In some embodiments, the piezoelectric element(s) 312 may respond to ultrasound energy transmissions within a particular frequency range, e.g., 500 kHz to 10 MHz, 800 kHz to 2 MHz, or 950 kHz to 1 MHz. The piezoelectric element(s) 312 can include crystal, ceramic, and/or other materials configured to accumulate electrical charge in response to receiving ultrasound energy. Accordingly, the piezoelectric element(s) 312 are configured to generate an electric charge in response to receiving the ultrasound energy via the IPG 120 (FIG. 1) or diagnostic sources. The generated electric charge can be delivered to the circuit 320 via the diodes 314, e.g., along the first and second pathways. In some embodiments, the diodes 314 can be Zener diodes or other components configured to limit the output voltage delivered to the circuit 320 to a predetermined maximum cardiac pacing pulse voltage (e.g., less than 2.8 V). In other embodiments separate circuit components are used to limit or clamp the output voltage level. In some embodiments, the diodes are Schottky diodes which have a low forward voltage for energy efficiency.

Figure 4:
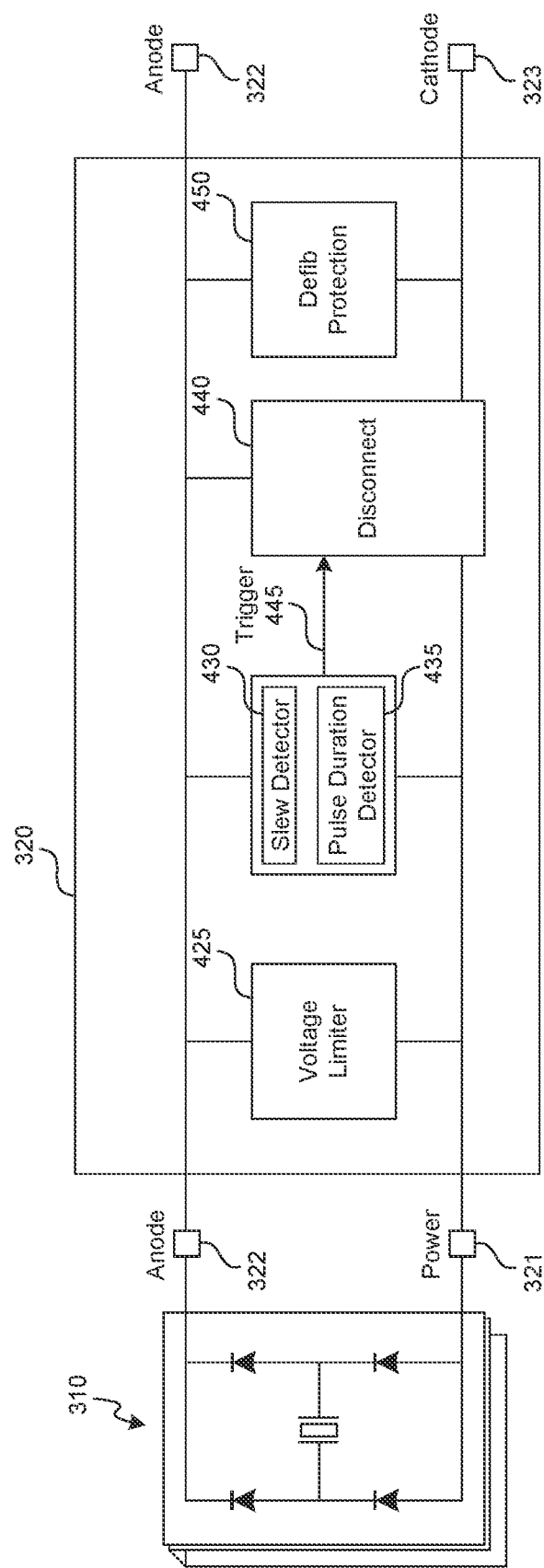
FIG. 4 is a schematic diagram of embodiments of a circuit of the receiver-stimulator shown in FIG. 3, in accordance with the present technology.

FIG. 4 is a schematic diagram of an embodiment of a circuit 320 of the receiver stimulator 110 shown in FIG. 3, in accordance with the present technology. In addition to the features described in FIG. 3, the circuit 320 can include a voltage limiter 425, a slew rate detector 430, a pulse duration detector 435, and a disconnect 440 operably coupled to each of the slew rate detector 430 and the pulse duration detector 435. The circuit 320 can also include defib protection 450 to protect the circuit from damage due to high voltage generated between the anode 322 and cathode 323 during defibrillation.

The voltage limiter 425 can be formed from p-n junction diodes in series or include a shunting switch formed from metal-oxide-semiconductor (MOS) devices such that it limits the input voltage received at the circuit 320 to be less than a preset amount. For example, the voltage limiter 425 can limit the voltage to a maximum cardiac pacing pulse voltage (e.g., less than about 3V). In some embodiments, the upper voltage limit of the voltage limiter 425 may be slightly lower than the upper reverse voltage limit of the diodes 314 (FIG. 3) which, as previously described, can also be configured to limit the input voltage.

The defib protection 450 protects the circuit in the case of high voltage defibrillation shocks. A defibrillation event can cause a voltage to develop between the anode and cathode. While the circuit 320 is protected from a positive voltage between the anode and cathode via the voltage limiter 425, it is also desirable to protect the circuit 320 from a negative voltage between the anode and cathode. Accordingly, the defib protection 450 can include a reverse-biased diode configured to absorb such a negative voltage.

The slew rate detector 430 can be configured to detect whether the rate of change of the input voltage signals ("voltage rate") received from the components 310 exceeds a predetermined threshold. The predetermined threshold voltage rate of the slew rate detector 430 can be set to be less than an expected voltage rate of voltage signals corresponding to ultrasound energy signals not intended for cardiac pacing, and above the expected voltage rate of voltage signals corresponding to ultrasound energy signals intended for cardiac pacing. Accordingly, the slew rate detector 430 is configured to detect signals from conventional ultrasound imaging 212, while not detecting signals intended for cardiac pacing 232. For example, as previously described with reference to FIG. 2, the voltage rate 214 of an individual pulse corresponding to the conventional diagnostic waveform (e.g., conventional waveform 212) can be approximately 1.5 V/μs, whereas the voltage rate 234 of an individual pulse corresponding to waveforms (e.g., waveform 232) of the present technology can be approximately 0.075 V/μs. Accordingly, a predetermined threshold voltage rate set above about 0.1 V/μs, 0.3 V/μs, 0.4 V/μs, 0.5 V/μs, 0.8 V/μs, 1.0 V/μs, or greater depending on the expected voltage rate of the diagnostic waveform, would be suitable to detect signals not intended for cardiac pacing, while not detecting signals intended for cardiac pacing.

The pulse duration detector 435 can be configured to detect whether a pulse duration of an individual pulse of input voltage signals received from the components 310 exceeds a predetermined threshold time. The predetermined threshold time of the pulse duration detector 435 can be set to be less than an expected pulse duration of voltage signals corresponding to continuous wave ultrasound imaging systems, and above the expected maximum pulse duration of voltage signals corresponding to ultrasound energy signals intended for cardiac pacing. Accordingly, the pulse duration detector 435 is configured to detect continuous or long-duration signals not intended for cardiac pacing, while not detecting signals intended for cardiac pacing. For example, as described with reference to FIG. 2, the pulse duration 226 of an individual pulse corresponding to the conventional continuous diagnostic waveform (e.g., conventional waveform 222) can be about 20 milliseconds (ms) or greater, whereas the pulse duration 236 of an individual pulse corresponding to waveforms (e.g., waveform 232) of the present technology can be approximately 19 microseconds (μs) to 4.4 ms. Accordingly, a predetermined threshold time set above about 1 ms, 5 ms, 10 ms, 20 ms, or greater (e.g., 100 ms or 200 ms) depending on the pacing pulse width of the system, would be suitable to detect signals not intended for cardiac pacing, while not detecting signals intended for cardiac pacing to be delivered to the patient in the form of electrical stimulation.

As shown in FIG. 4, the slew rate detector 430 and pulse duration detector 435 are operably coupled to the disconnect 440. The main function of the disconnect 440 is to electrically disconnect the cathode 323 from the power 321 if either the slew rate detector 435 or pulse duration detector 435 detect an ultrasound signal that is not intended for cardiac pacing and otherwise electrically connect the cathode 323 and power 321. The disconnect 440 can also include a latch mechanism such that a transient detection causes electrical disconnection of the power and cathode lines to continue for the remaining duration of the input waveform. The disconnect 440 can also include a memory element such that the electrical disconnection persists after the input waveform ends and the circuit is no longer active, e.g. the power line 321 is at the same electrical potential as the anode line 322. In this way the power 321 and cathode 323 will remain electrically disconnected between a series of separate input waveforms. Furthermore, the disconnect may reconnect the power 321 and cathode 323 and clear the memory element in response to an input waveform that is intended for cardiac pacing.

Figure 5:
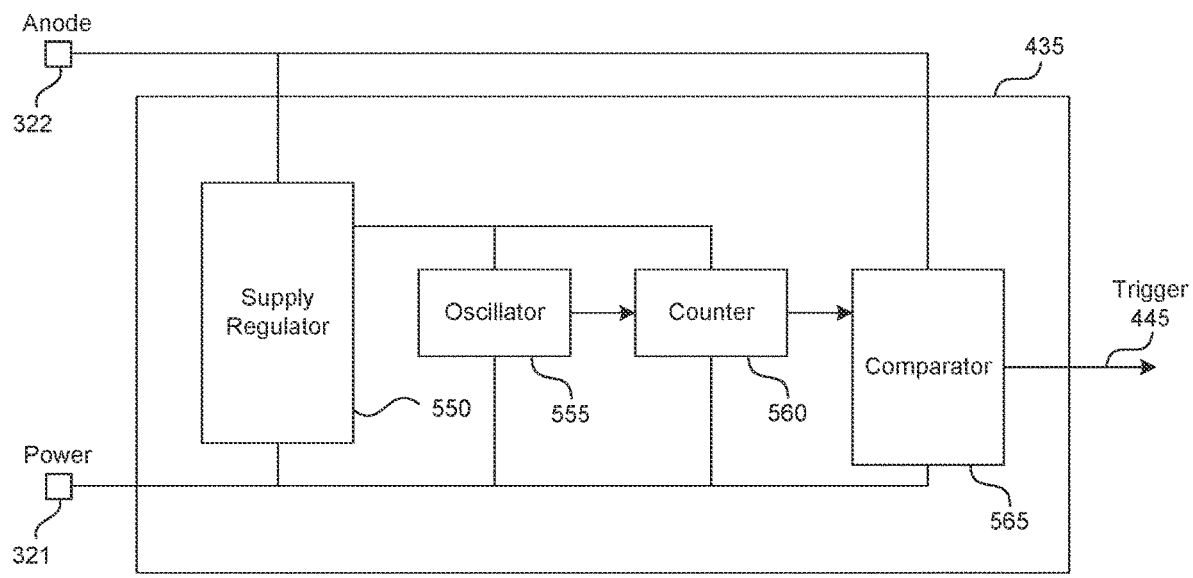
FIG. 5 is a schematic diagram of a pulse duration detector used in the accordance with the present technology.

FIG. 5 shows additional detail of an embodiment of the pulse duration detector 435. The pulse duration detector 435 can also include a supply regulator 550, an oscillator 555, a counter 560, and comparator 565. Together, these components can correspond to the pulse duration detector 435 previously described in FIG. 4. The supply regulator 550 receives an input voltage formed between the power 321 and the anode 322. Note the power 321 is at lower voltage than the anode 322 in a typical application. The supply regulator 550 is configured to supply a voltage (e.g., 0.5 V) to the oscillator 555 having less variation than the voltage of the input voltage signals received by the supply regulator 550. The supply regulator 550 reduces variations in oscillator frequency and thus improves the accuracy of pulse duration measurement. The oscillator 550 drives a counter 560 (e.g., a ripple counter). The comparator 565 compares the value of the counter 560 to a predetermined value. The comparator output is normally at anode 322 potential. If the counter value matches the value in the comparator 565, the output of the comparator is pulled down to the power 321 potential indicating the detection of a long duration pulse. The output of the comparator, trigger 445, is connected to the disconnect 440 and acts to trigger the disconnect 440.

Figure 6:
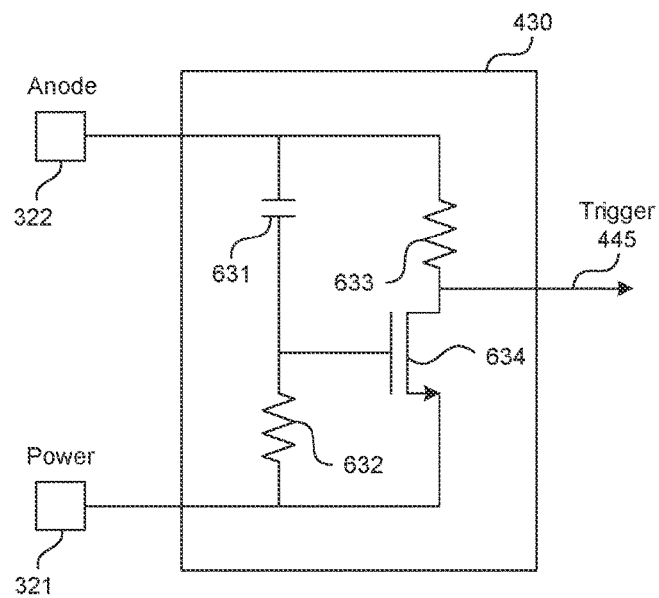
FIG. 6 is a schematic diagram of slew rate detector used in accordance with the present technology.

FIG. 6 is a schematic diagram of an embodiment of the slew rate detector 430 of the circuit 320 shown in FIG. 4, in accordance with embodiments of the present technology. The slew rate detector 430 has reference voltages from the anode 322 and power 321 with the power 321 being at a lower potential than the anode 322. In response to a high slew rate input the voltage across capacitor 631 will increase more slowly than the voltage across resistor 632 causing an FET 634 to conduct, which in turn causes current to flow through a resistor 633 producing the trigger output 445 to decrease down close to the potential of the power 321. For low slew rate signals the voltage across the capacitor 631 will be greater than the voltage across the resistor 632, which prevents the FET 634 from conducting and in turn pulls the trigger 445 up to the potential of the anode 322. The threshold for slew rate detection can thus be adjusted by changing the value for the resistor 632 or capacitor 631.

Figure 7:
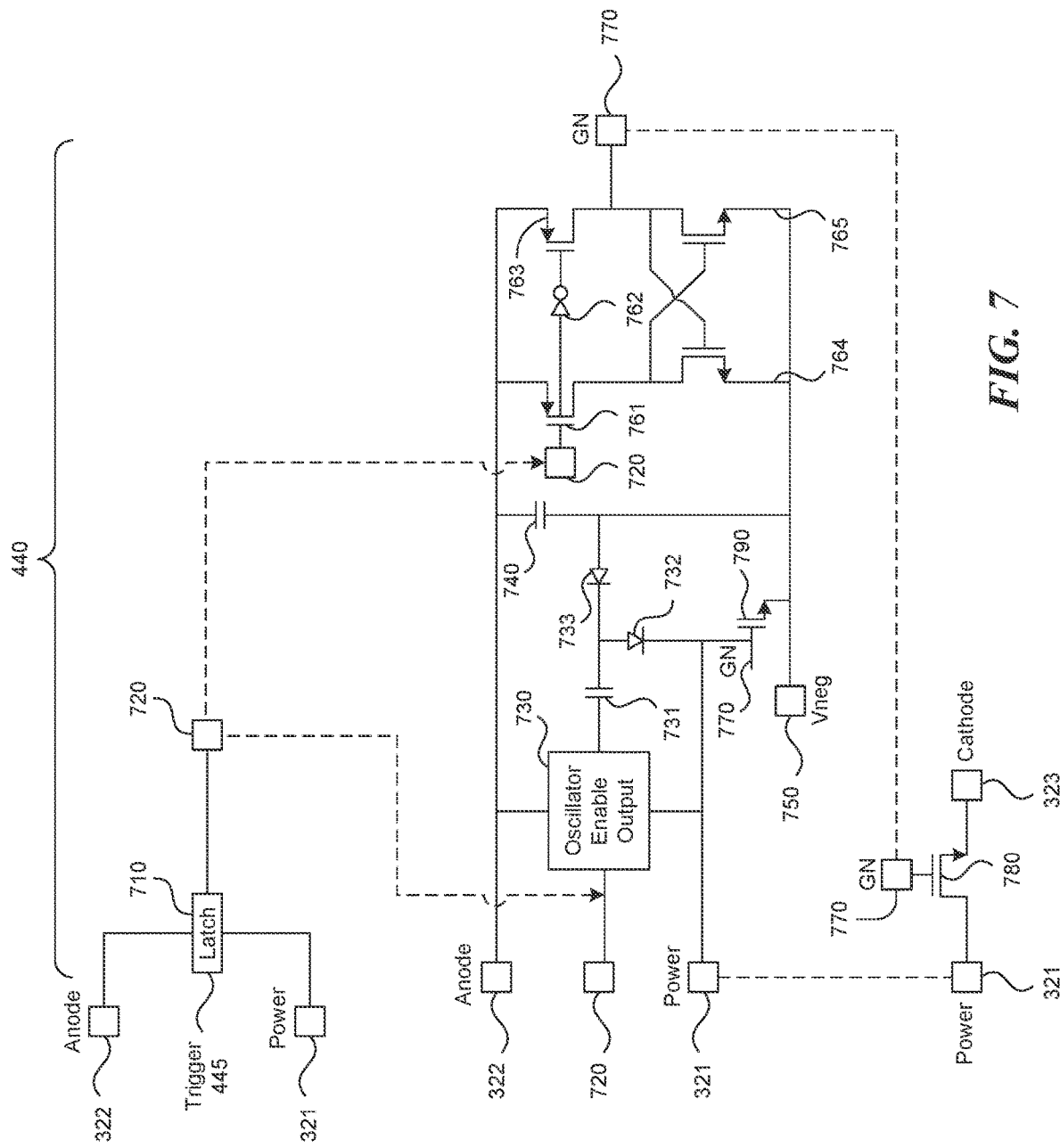
FIG. 7 is a schematic diagram of disconnect circuit used in accordance with the present technology.

FIG. 7 is a schematic diagram of an embodiment of the disconnect 440 shown in FIG. 4. The anode 322 and power 321 provide the supply voltage for the circuit with the power 321 being at a lower potential than the anode 322. A latch 710 provides a latch function such that if the trigger output 445 from either the slew rate detector 430 or pulse duration detector 435 is pulled to a low potential at or near power 321, a latch output 720 will drop to at or near the power 321 and remain there until the voltage on the power 321 rises to a voltage near the anode voltage 322 (i.e. when the circuit loses power due to the lack of an input waveform). The latch output 720 is connected to an oscillator 730 and a FET 761. The latch output 720 can be connected to other types of transistors (e.g., BJTs). When the latch output 720 drops to the power voltage 321, the oscillator 730 is enabled. The oscillator 730 output drives a charge pump formed by diodes 732 and 733, and capacitors 731 and 740. The charge pump creates a potential, indicated by node VNEG 750, across a capacitor 740 that is lower than the power voltage 321. A number of FETS 761, 763, 764, 765 and an inverter 762 form a level shifter. When the latch output 720 drops to the power voltage, the level shifter drops the output node GN 770 from the anode potential 322 to the voltage VNEG 750 which can be lower than the power voltage 321. The output node GN 770 is connected to the main disconnect switch 780, which electrically disconnects the power 321 and the cathode 323. The disconnect switch 780 can be an NMOS depletion mode device that, in a non-powered state, defaults to on with a low impedance path between power 321 and the cathode 323. However, to switch off an NMOS depletion device, i.e. create a high impedance between power 321 and the cathode 323, a voltage must be applied to the gate that is lower than both the drain and source voltages, which in this case is provided by the charge pump and level shifter features of the circuit. If the depletion switch 780 is turned off in response to an input signal that has either a high slew rate or long pulse duration, the voltage VNEG 750 will remain stored on the capacitor 740 after the input signal has ended and the power 321 has risen to the level of the anode 322. This is because there is no discharge path for the voltage on capacitor 740. This will cause the gate voltage 770 to remain at a low potential keeping the depletion switch 780 open after the input signal has ended.

In this way the capacitor 740 provides a memory element that retains switch state after the input signal has ended. This is advantageous because ultrasound imaging systems generate sequential transmissions directed out at different angles to form a single image frame. Typically one frame will generate multiple input signals separated in time as the transmit angle sweeps through the location of the electrode. The first signal to intersect the electrode and trigger the slew rate detector 430, will cause the depletion switch 780 to open. However, a portion of this initial signal will pass through because there is a time delay for the slew rate detector 430 to trigger and the charge pump to generate a large negative voltage to ultimately open the depletion switch 780. This allows the leading edge of the initial pulse to pass through, but in the disconnect 440 shown in FIG. 7 this only occurs for the first pulse. The leading edge and other portions of subsequent pulses are completely blocked by this embodiment of the disconnect 440. More specifically, without the memory provided by the capacitor 740, the leading edge of every pulse from the imaging system would be passed through. Once the depletion switch 780 is open and VNEG 750 is stored on the capacitor 740, i.e. the memory is stored or set, if an input signal comes in that does not trigger the slope detector, the circuit will power up with the latch output 720 at the voltage potential of the anode 322. This will cause the FET 763 in the level shifter to conduct, which causes the node GN 770 to drop to the anode voltage 321 that in turn closes the depletion switch 780 allowing the remaining portion of the slow slew-rate signal to pass through to the cathode 323. Additionally, the node GN 770 is also connected to the FET 790 so that when node GN 770 drops to the anode potential, then the FET 790 will start to conduct causing the capacitor 740 to discharge which in turn drops VNEG 750 to the power potential 321. In some embodiments, the system can have a separate switch for the slew rate and the pulse duration.

Figure 8:
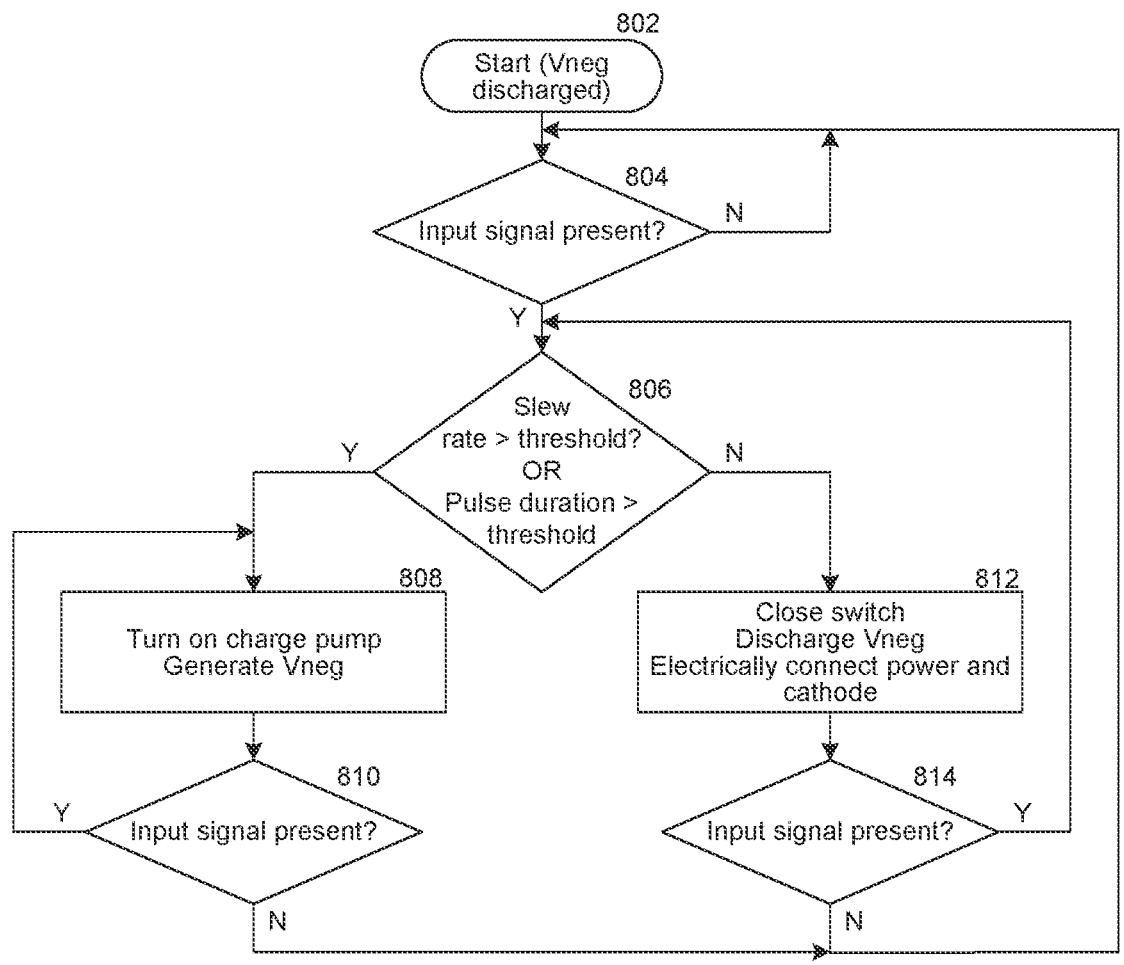
FIG. 8 is a flow chart corresponding to a process for operating the receiver-stimulator shown in FIG. 1 in accordance with the present technology.

FIG. 8 is a flow chart corresponding to a process 800 for operating the receiver 110. The process starts at node 802 with VNEG discharged. In process node 804, the system is idle and looping until a signal is present, which causes transition to node 806 where the system is detecting the presence of either a high slew rate or long pulse duration. If either the slew rate or the pulse duration exceeds the respective threshold, the process transitions to node 808 where the trigger event is latched, which turns on the charge pump to generate a voltage VNEG that is below the potential of the power 321. This electrically disconnects the power 321 from the cathode. The system will remain in this state at node 810 with charge pump actively generating VNEG as long as the input signal is present. Once the signal is no longer present the process transitions back to node 804 with VNEG maintained and the switch disconnected. Once an input signal is present, the process returns to node 806. If there is no high slew rate or long pulse duration detection then the process will proceed to node 812 and discharge VNEG, causing electrical disconnection of the power 321 and cathode 323. This would be the case for a low slew rate signal intended for pacing following a high slew rate or long pulse duration signal for ultrasound imaging. The process then returns to node 814 which returns the process to node 806 if there is still an input signal present. This allows for the detection of later portions of the same signal that may exceed the slew rate or pulse duration thresholds. If there is no longer a signal present, the process returns to node 804 with the VNEG discharged and the power 321 electrically connected to the anode 323.

Figure 9:
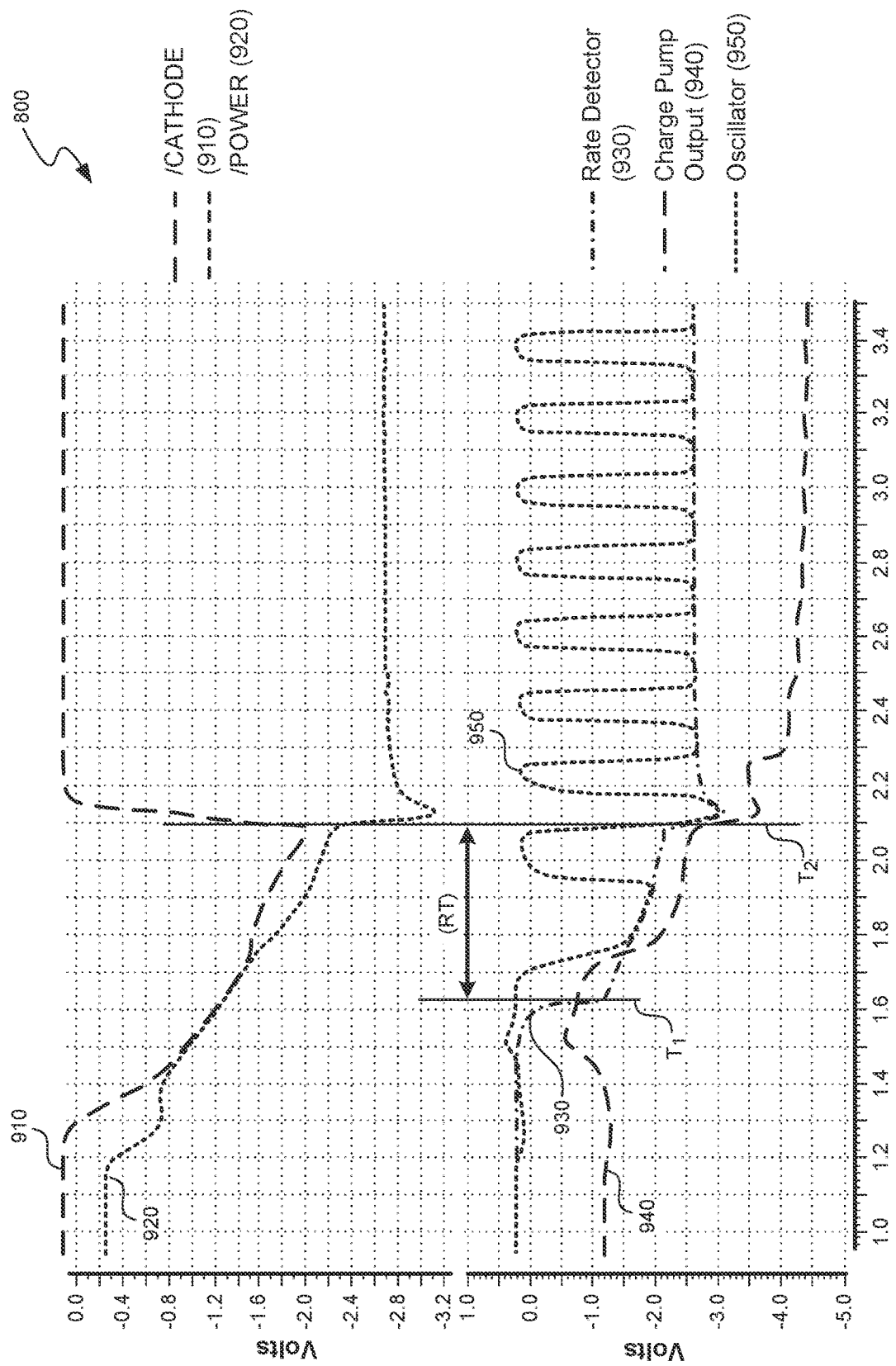
FIG. 9 is a plot corresponding to operation of the receiver-stimulator shown in FIG. 1, in accordance with the present technology.

FIG. 9 is a plot 900 corresponding to operation of the receiver 110 in accordance with embodiments of the present technology. Plot 900 includes multiple lines, including (a) line 910 corresponding to output voltage at the cathode (i.e., at the third pin 323), (b) line 920 corresponding to the power voltage provided to the circuit (i.e., at the first pin 321), (c) line 930 corresponding to the output of the slew rate detector 720, (d) line 940 corresponding to voltage output of the charge pump (VNEG 750), and (e) line 950 corresponding to voltage output from the oscillator 730. Line 920 can correspond to a signal generated in response to diagnostic ultrasound, or other types of signals not intended for cardiac pacing and having a corresponding fast voltage rate. As shown in FIG. 9, line 920 indicates that a signal having a fast voltage rise rate is received when time equals about 1.25 µs. As line 920 decreases with time, line 910 also begins to decrease with time. When time equals about 1.50 µs, line 930 corresponding to the slew rate detector also begins to decrease with time, and at time ($T_1$) (i.e., when time equals about 1.63 µs), the slew rate detector trips. At time ($T_1$), the conductive channel of the FET of the slew rate detector is created, the stored charge of the slew rate detector is delivered to the charge pump via the conductive channel, and the charge pump is thereby enabled. Additionally, as indicated by line 950, the oscillator of the charge pump is enabled after the slew rate detector trips, and negative voltage begins to build at the main switch. As shown in FIG. 9, line 940 corresponding to the charge pump voltage output includes a relatively rapid decrease in voltage between times at 1.7-1.8 µs, and a more gradual decrease in voltage between times at 1.8-2.0 µs. The rapid voltage decrease can correspond to stored voltage on a capacitor being discharged after the slew rate detector trips, and the subsequent gradual voltage decrease can correspond to additional negative voltage generated by the oscillator. At time ($T_2$), the main switch opens, thereby disconnecting the cathode from the input voltage signals and preventing delivery of the input voltage signals to the patient in the form of electrical stimulation. Accordingly, after the main switch opens, line 910 corresponding to the output voltage at the cathode rises to approach zero volts, and line 920 corresponding to the input voltage decreases rapidly, but then settles at about 2.8V due to the voltage limiter. As shown in FIG. 9, the response time (RT) between times ($T_1$) and ($T_2$) is about 470 nanoseconds. Accordingly, the voltage signals received more than about 470 nanoseconds after the slew rate detector trips are prevented from being delivered to the patient in the form of electrical stimulation.

Figure 10:
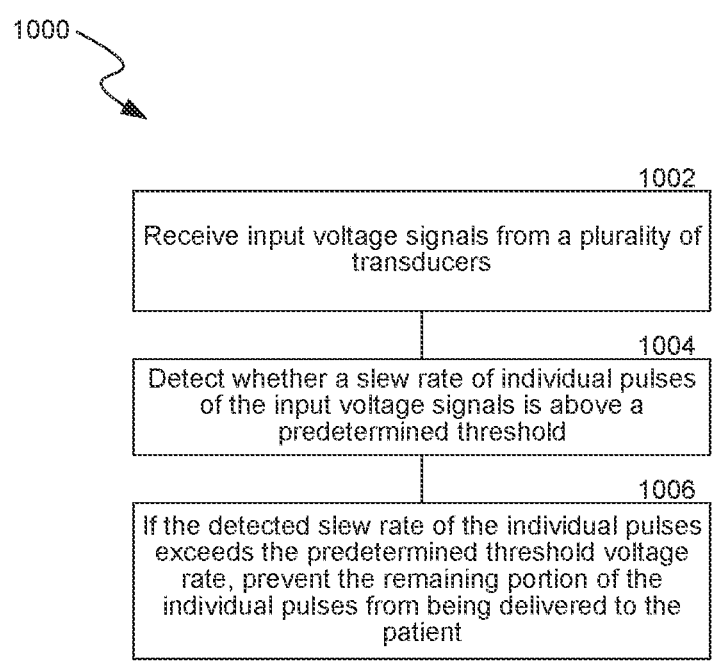
FIG. 10 is a block diagram illustrating a process for delivering stimulation pulses to a patient via the implantable medical device system shown in FIG. 1.

FIG. 10 is a block diagram illustrating a process for delivering stimulation pulses to a patient via the implantable medical device system shown in FIG. 1. Process 1000 includes receiving input voltage signals from a plurality of transducers (process portion 1002), and detecting whether a voltage rate of individual pulses of the input voltage signals is above a predetermined threshold voltage rate (process portion 1004). The input voltage signals can be produced in response to ultrasound energy received by the plurality of transducers. Process 1000 further includes, if the detected voltage rate of the individual pulses exceeds the predetermined threshold voltage rate, preventing the corresponding individual pulses from being delivered to the patient (process portion 1006) in the form of electrical stimulation. In some embodiments, the medical device system can include a normally-closed main switch, and preventing the corresponding pulses from being delivered to the patient can include moving the switch to an open position in response to the detected voltage rate exceeding the predetermined threshold voltage rate. In some embodiments, preventing the corresponding individual pulses from being delivered to the patient can include (a) enabling a charge pump if a gate voltage of an n-type transistor device exceeds a threshold voltage of the n-type transistor device, and (b) moving the switch to an open position in response to the charge pump being enabled.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

As used herein, "generally," "approximately," or "about" when preceding a value, should be interpreted to mean plus or minus 10% of the value, unless otherwise indicated.

To the extent that any of the foregoing patents, published applications, and/or other materials incorporated herein by reference conflict with present disclosure, the present disclosure controls.

The subject technology is illustrated, for example, according to various aspects described below. Various examples of aspects of the subject technology are described as numbered examples (1, 2, 3, etc.) for convenience. These are provided as examples and do not limit the subject technology. It is noted that any of the dependent examples may be combined in any combination, and placed into a respective independent example, (e.g., examples 1, 17 or 25). The other examples can be presented in a similar manner.

Examples

1. An implantable medical device system, comprising:
a housing;
electrodes carried by the housing;
a transducer within the housing and configured to produce input voltage signals in response to receiving ultrasound energy; and
a circuit electrically coupled to the transducer and within the housing, wherein the circuit is configured to receive the input voltage signals and provide output voltage signals via an electrical pathway comprising the electrodes, the circuit including—
  a switch on the electrical pathway, wherein the switch has an open state and a closed state; and
  a slew rate detector configured to detect whether a voltage rate of an individual pulse of the input voltage signals exceeds a predetermined threshold rate,
wherein the circuit is configured to change the switch from the closed state to the open state in response to the detected voltage rate exceeding the predetermined threshold rate.

2. The system of example 1 wherein the circuit further comprises a charge pump configured to generate a negative voltage in response to the detected voltage rate exceeding than the predetermined threshold rate, wherein the generated negative voltage causes the switch to move to the open position.

3. The system of example 2 wherein the charge pump comprises an oscillator, a voltage inverter, and a semiconductor device.

4. The system of any of examples 1-3 wherein the slew rate detector comprises a resistor, a capacitor in series with the resistor, and an transistor device.

5. The system of example 4 wherein the transistor device has a gate voltage and a threshold voltage, and wherein the n-type transistor is configured such that the gate voltage exceeds the threshold voltage at the predetermined threshold rate.

6. The system of any of examples 1-5 wherein the predetermined threshold rate is equal to or greater than about 0.5 V/microsecond.

7. The system of any of examples 1-6 wherein the transducer comprises a piezoelectric element.

8. The system of any of examples 1-7, further comprising a die including the circuit, the die having a first dimension of about 500 micrometers or less, a second dimension of about 1500 micrometers or less, and a third dimension of about 250 micrometers or less.

9. The system of any of examples 1-8 wherein the circuit further comprises a voltage limiter configured to inhibit the input voltage from increasing above about 3V.

10. The system of any of examples 1-9 wherein the electrodes include a ring electrode in electrical communication with the housing, and a tip electrode positioned to deliver the output voltage signals to a patient.

11. The system of any of examples 1-10 wherein the circuit further comprises a pulse duration detector, wherein the pulse duration detector is configured to detect a pulse duration of the individual pulses of the input voltage signals, and wherein the switch moves to the open position in response to the detected pulse duration exceeding a predetermined threshold time.

12. The system of example 11 wherein the pulse duration detector is in parallel with the slew rate detector and comprises (a) an oscillator, (b) a regulator configured to receive the input voltage signals and provide a stable supply voltage to the oscillator, and (c) a counter set to correspond to the predetermined threshold time 13. The system of any of examples 11 or 12 wherein the predetermined threshold time is greater than about 20 milliseconds.

14. The system of any of examples 11-13 wherein the circuit further comprises a charge pump configured to generate a negative voltage in response to the detected pulse duration exceeding the predetermined threshold time, wherein the generated negative voltage causes the switch to move to the open position.

15. The system of any of examples 1-14 wherein the switch is a normally-closed switch.

16. The system of any of examples 1-15 wherein the housing is configured to be attached to the left ventricle of a patient's heart.

17. A method for providing stimulation pulses to a patient via an implantable medical device system, comprising:
receiving input voltage signals from a plurality of transducers, the input voltage signals being produced in response to ultrasound energy received by the transducers;
detecting whether a voltage rate of individual pulses of the input voltage signals exceeds above a predetermined threshold rate; and if the detected voltage rate of the pulses exceeds the predetermined threshold rate, preventing the corresponding pulses from being delivered to the patient in the form of electrical stimulation.

18. The method of example 17 wherein the medical device system includes a normally-closed switch, and wherein preventing the corresponding individual pulses from being delivered to the patient comprises moving the normally-closed switch to an open position in response to the detected voltage rate exceeding the predetermined threshold rate.

19. The method of any of examples 17 or 18 wherein the medical device system includes a switch, and wherein preventing the corresponding individual pulses from being delivered to the patient comprises:
generating a negative voltage in response to the determined voltage rate exceeding the predetermined threshold rate; and
moving the switch to an open position in response to the generated negative voltage, wherein moving the switch to the open position prevents delivery of the individual pulses to the patient.

20. The method of any of examples 17-19 wherein the medical device system comprises a transistor device, and a switch along an electrical pathway for providing the individual pulses to the patient, and wherein preventing the corresponding individual pulses from being delivered to the patient comprises:
enabling a charge pump if a gate voltage of the n-type transistor device exceeds a threshold voltage of the n-type transistor device; and
moving the switch to an open position in response to the charge pump being enabled.

21. The method of any of examples 17-20, further comprising providing output voltage signals corresponding to the input voltage signals to the patient, wherein:
receiving the input voltage signals from the transducer occurs via a first electrode, and;
providing the output voltage signals occurs via a second electrode in direct electrical communication with the patient's heart.

22. The method of any of examples 17-21 wherein preventing the corresponding individual pulses from being delivered to the patient occurs when a pulse duration of the individual pulses exceeds a predetermined threshold time.

23. The method of example 22 wherein the predetermined threshold rate is 0.2 V/microsecond and the predetermined threshold time is 20 milliseconds.

24. The method of any of examples 22 or 23 wherein the medical device system includes a switch, and wherein preventing the corresponding individual pulses from being delivered to the patient comprises:
generating a negative voltage in response to (a) the pulse duration of the pulses exceeds the predetermined threshold time, or (b) the determined voltage rate exceeding the predetermined threshold rate; and
moving the switch to the open position in response to the generated negative voltage, wherein moving the switch to the open position prevents delivery of the pulses to the patient.

25. A cardiac synchronization system, comprising:
a programmer;
an implantable pulse generator (IPG) in operable communication with the programmer and configured to generate ultrasound energy;
a receiver-stimulator in operable communication with at least one of the programmer or the IPG, wherein the receiver-stimulator is configured to (a) be implanted at or proximate to a patient's heart and (b) provide stimulation signals to the patient's heart, the receiver-stimulator including—
a piezoelectric element configured to produce the stimulation signals in response to the ultrasound energy generated from at least one of the IPG or an external source;
a first terminal in electrical communication with the piezoelectric element;
a second terminal configured to be in electrical communication with the patient's heart;
a circuit electrically coupled to the first terminal, and configured to provide the stimulation signals to the patient's heart via an electrical pathway comprising the second terminal, wherein the circuit includes—
a slew rate detector configured to detect whether a voltage rate of individual stimulation signals exceeds a predetermined threshold rate
wherein the circuit is configured to electrically decouple the first terminal from the second terminal if a voltage rate of individual stimulation pulses is greater than the predetermined threshold rate.

26. The system of example 25 wherein the circuit further includes a switch on the electrical pathway, and wherein the circuit is configured to electrically decouple the first terminal from the second terminal by moving the switch to an open position.

27. The system of example 26 wherein the slew rate detector comprises a resistor, a capacitor in series with the resistor, and an n-type transistor device having a gate voltage and a threshold voltage, wherein the n-type transistor is configured such that the gate voltage exceeds the threshold voltage at the predetermined threshold rate, and wherein the circuit further includes a charge pump configured to generate a negative voltage at the switch if the gate voltage exceeds the predetermined threshold voltage.

28. The system of any of examples 25-27 wherein the IPG includes a battery module and the receiver does not include a battery module.

I claim:
1. An implantable medical device system, comprising:
a housing;
electrodes carried by the housing;
a transducer within the housing and configured to produce input voltage signals in response to receiving ultrasound energy; and
a circuit electrically coupled to the transducer and the electrodes, wherein the circuit is configured to—
detect whether a slew rate of an individual pulse of input voltage signals received by the circuit exceeds a predetermined threshold rate; and
when the detected slew rate exceeds the predetermined threshold rate, prevent the corresponding pulse of the input voltage signals from being delivered to the electrodes.

2. The system of claim 1 wherein the circuit comprises a slew rate detector configured to detect whether the slew rate of the individual pulse of the input voltage signals exceeds the predetermined threshold rate.

3. The system of claim 2 wherein the slew rate detector comprises a resistor, a capacitor in series with the resistor, and a transistor device.

4. The system of claim 1 wherein the predetermined threshold rate is equal to or greater than about 0.5 Volt per microsecond.

5. The system of claim 1 wherein:
the ultrasound energy comprises diagnostic ultrasound energy and cardiac pacing ultrasound energy;
a slew rate of the diagnostic ultrasound energy is greater than the predetermined threshold rate, and
a slew rate of the cardiac pacing ultrasound energy is less than the predetermined threshold rate.

6. The system of claim 5 wherein the slew rate of the diagnostic ultrasound energy is greater than about 1 Volt per microsecond.

7. The system of claim 5 wherein the slew rate of the cardiac pacing ultrasound energy is less than about 0.1 Volt per microsecond.

8. The system of claim 1 wherein the circuit comprises a switch configured to open to prevent the corresponding pulse of the input voltage signals from being delivered to the electrodes when the detected slew rate exceeds the predetermined threshold rate.

9. The system of claim 8 wherein the circuit is further configured to generate a negative voltage in response to the detected slew rate exceeding the predetermined threshold rate, and wherein the generated negative voltage is configured to cause the switch to move to the open position.

10. An implantable medical device system, comprising:
electrodes;
a transducer electrically coupled to the electrodes and configured to produce input voltage signals in response to receiving ultrasound energy; and
a circuit electrically coupled to the transducer and the electrodes, wherein the circuit is configured to—
receive the input voltage signals;
detect whether a slew rate of an individual pulse of the input voltage signals exceeds a predetermined threshold rate;
detect whether a pulse duration of the individual pulse of the input voltage signals exceeds a predetermined threshold time; and
when either the detected slew rate exceeds the predetermined threshold rate or the detected pulse duration exceeds the predetermined threshold time, prevent the corresponding pulse of the input voltage signals from being delivered to the electrodes.

11. The system of claim 10 wherein the circuit comprises a pulse duration detector configured to detect whether the pulse duration of the individual pulse of the input voltage signals exceeds the predetermined threshold rate.

12. The system of claim 11 wherein the pulse duration detector comprises (a) an oscillator, (b) a regulator configured to receive the input voltage signals and provide a stable supply voltage to the oscillator, and (c) a counter set to correspond to the predetermined threshold time.

13. The system of claim 10 wherein the predetermined threshold time is equal to or greater than about 20 milliseconds.

14. The system of claim 10 wherein the ultrasound energy comprises diagnostic ultrasound energy and cardiac pacing ultrasound energy, wherein the pulse duration of the diagnostic ultrasound energy is greater than the predetermined threshold time, and wherein the pulse duration of the cardiac pacing ultrasound energy is less than the predetermined threshold time.

15. The system of claim 10 wherein the circuit comprises a switch configured to open to prevent the corresponding pulse of the input voltage signals from being delivered to the electrodes when the detected pulse duration exceeds the predetermined threshold time.

16. The system of claim 15 wherein the circuit is further configured to generate a negative voltage in response to the detected pulse duration exceeding the predetermined threshold time, and wherein the generated negative voltage is configured to cause the switch to move to the open position.

17. The system of claim 15 wherein the switch is normally in a closed position.

18. The system of claim 10 wherein the predetermined threshold rate is equal to or greater than about 0.5 Volt per microsecond, and wherein the predetermined threshold time is equal to or greater than about 20 milliseconds.

19. The system of claim 10 wherein the circuit comprises a switch configured to open to prevent the corresponding pulse of the input voltage signals from being delivered to the electrodes when either the detected voltage rate exceeds the predetermined threshold rate or the detected pulse duration exceeds the predetermined threshold time.

* * * * *